(12) United States Patent
Beer et al.

(10) Patent No.: US 8,051,716 B2
(45) Date of Patent: Nov. 8, 2011

(54) METHOD FOR TESTING A BEARING COMPONENT BY MEANS OF ULTRASOUND AND OPTICAL INSPECTION

(75) Inventors: Oskar Beer, Landshut (DE); Edgar Streit, Poppenlauer (DE)

(73) Assignee: Schaeffler KG, Herzogenaurach (DE)

( * ) Notice: Subject to any disclaimer, the term of this patent is extended or adjusted under 35 U.S.C. 154(b) by 404 days.

(21) Appl. No.: 12/441,498

(22) PCT Filed: Sep. 12, 2007

(86) PCT No.: PCT/DE2007/001641
§ 371 (c)(1),
(2), (4) Date: Mar. 16, 2009

(87) PCT Pub. No.: WO2008/031423
PCT Pub. Date: Mar. 20, 2008

(65) Prior Publication Data
US 2009/0308162 A1    Dec. 17, 2009

(30) Foreign Application Priority Data
Sep. 16, 2006  (DE) .......................... 10 2006 043 570

(51) Int. Cl.
*G01M 13/02* (2006.01)
*G01B 11/24* (2006.01)
(52) U.S. Cl. ....................................... 73/593; 356/601

(58) Field of Classification Search ........................ None
See application file for complete search history.

(56) References Cited

U.S. PATENT DOCUMENTS

| 4,011,748 A | * | 3/1977 | Bond et al. ...................... 73/601 |
| 5,005,417 A | * | 4/1991 | Kawasaki et al. ............... 73/593 |
| 5,257,544 A | * | 11/1993 | Khuri-Yakub et al. ......... 73/579 |
| 6,062,084 A | | 5/2000 | Chang et al. |

FOREIGN PATENT DOCUMENTS

| EP | 1 302 769 A | 4/2003 |
| WO | 02/44709 A | 6/2002 |

* cited by examiner

*Primary Examiner* — Harshad Patel
(74) *Attorney, Agent, or Firm* — Lucas & Mercanti, LLP

(57) ABSTRACT

A method for testing a bearing component in order to ensure that the bearing surface and a load-bearing region located underneath the bearing surface are in a perfect condition. A material testing depth containing the point of maximum mechanical load during operation is determined. In a first partial testing step, the bearing component is subjected to an ultrasound test by which the material region underneath the bearing surface is tested for defects by ultrasound, at least up to the material testing depth. In a second partial testing step, a full optical test of the bearing surface is carried out During the second partial testing step, the actual surface state of the bearing surface is compared with a nominal surface state. The bearing component is then only classified as faultless if the results of the two partial testing steps do not reveal any defects.

2 Claims, 5 Drawing Sheets

Fig. 4
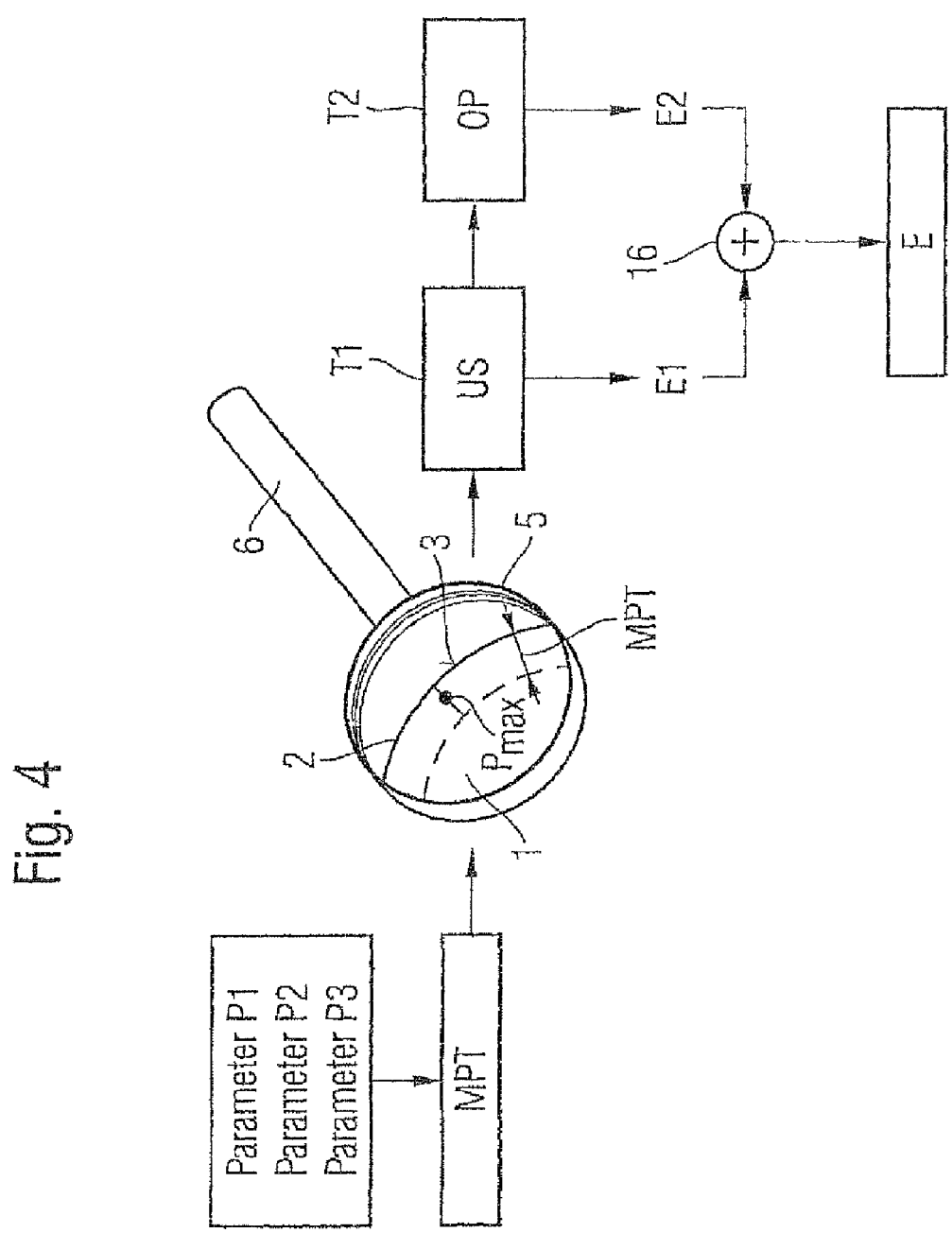
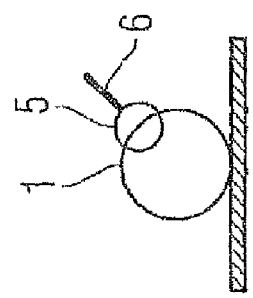

METHOD FOR TESTING A BEARING COMPONENT BY MEANS OF ULTRASOUND AND OPTICAL INSPECTION

This application is a 371 of PCT/DE2007/001641 filed Sept. 12, 2007, which in turn claims the priority of DE 10 2006 043 570.2 filed Sept. 16, 2006, the priority of both applications is hereby claimed and both applications are incorporated by reference herein.

The invention is in the field of bearing components that are designed for instances of particularly critical and high stress use such as, for example, in aeronautics and aerospace. The term bearing component is to be interpreted widely in the scope of the present invention and comprises the load bearing parts of a bearing such as bearing rings and, in particular, antifriction bearing members, chiefly antifriction bearing balls.

Such bearing components are used, for example, in main shaft bearings of gas turbines and gearboxes, in bearings for helicopters and in drive units of carrier rockets. During operation, there they are exposed to extraordinarily high stresses, and must exhibit a reliable and wear-free operating behavior even under extreme environmental and/or operating temperatures in conjunction with high rolling and sliding stresses between the actual rolling members and the assigned raceways of corresponding bearing components and/or bearing rings.

Because of these extremely high stresses, there is the risk of the formation of cracks at flaws inside the material and subsequent crack migration at the highly stressed areas of the bearing component. The further loading of such microcracks that then occurs in operation, for example by overrolling in antifriction bearings, leads to a crack growth that can lead in the most unfavorable case to component failure. Metallurgical and/or material causes of the occurrence of such microcracks are, for example, inhomogeneities in the material, instances of damage to the material at the surface owing to processing, or at or in the area near the surface. In the case of the preferred fields of use, named at the beginning, for such bearings, it is to be understood that instances of bearing damage can lead to substantial complications there and instances of extremely high consequential damage.

Consequently, extremely high reliability or an insignificant likelihood of failure is required of such bearing components. In order to meet this requirement, the bearing components may be subjected to a perfect, nondestructive test. Consideration is given as test methods to so-called eddy current testing, dye penetration testing, magnetic crack testing and, if appropriate, individual instances of visual testing carried out by inspectors.

Such quality testing has been unsatisfactory to date, however. Some test methods such as, for example, eddy current testing or magnetic crack testing can be applied only in the case of metal bearing components [with eddy current testing it is usually only possible to implement a testing depth of the order of magnitude of 30 to 60 µm]. Also, common defects with an order of magnitude of from 50 µm cannot always be reliably detected.

With regard to the maximum detectable size of defects and type of defect, visual tests depend on the experience and capability of the tester and/or of the human eye.

In summary, using the known testing methods it is possible to detect microcracks, inclusions and inhomogeneities and/or flaws only at the surface or only as far as a relatively shallow depth below the surface.

However, depending on the operating conditions and state of lubrication of the bearing, in the case of the high performance bearing components mentioned at the beginning, it is to be expected that significant material loads occur in deeper material layers. Consequently, flaws and inhomogeneities hidden there can lead to formation of cracks. These flaws located at greater depths can be detected—if at all—by the above-named methods only when reaching during a comparatively large dimensions (so-called defect size).

Against this background, it is the object of the present invention to specify a method that reliably ensures that in the case of a tested bearing component it can be guaranteed, that both the bearing surface and a load bearing area lying therebelow are completely free of defects.

This object is achieved according to the invention by a method for testing a bearing component, in the case of which a material testing depth is determined within which lies the point of the maximum mechanical load occurring during operation, in a first partial testing step the bearing component is subjected to an ultrasound test with the aid of which the material area lying beneath the bearing surface is tested for defects by means of ultrasound at least as far as the material testing depth, in a second partial testing step a complete optical test of the bearing surface is undertaken in which the actual surface condition of the bearing surface is compared with an ideal surface condition, and the bearing component being classified as defect free only when both partial testing steps yield a defect free result.

A first substantial aspect of the invention consists in that a material testing depth is determined and fixed taking account of the particular configuration, design and the future field of use of the bearing component and the operating conditions prevailing in this case. The point of the maximum load occurring during operation lies within this material testing depth. Although this range can, of course, vary depending on the dimensioning of the bearing, case of use and, for example, nominal diameter of the bearing, common material testing depths fixed by the inventors are of the order of magnitude of up to approximately 400 µm.

A further substantial aspect of the invention consists in that—preferably in the case of a complete, that is to say perfect component test—the bearing component is firstly subjected to an ultrasound test in the first partial testing step. It is possible, in particular, to reliably establish with this ultrasound test whether defects lying underneath the bearing surface and reaching onto the material testing depth are present in the material range, specifically in a very finely resolved inspection range such that it is perfectly possible to detect defects with a size or a diameter of from approximately 50 µm.

The term defect is to be understood broadly the scope of the present invention and comprises, among others, but without being limited thereto, the flaws, mentioned at the beginning, that lead to microcracks such as, for example, inclusions, inhomogeneities and flaws.

Therefore, a substantial advantage of the inventive method consists in that ultrasound testing is capable of reliably detecting defects from a critical defect size (for example 50 µm) in the material down to the material testing depth. It is particularly advantageous in this case that the inventive method is suitable even for nonmagnetic and nonmetallic materials (for example ceramic) for the bearing components, since it is not based on electrical and/or magnetic operating principles.

In the second partial testing step, a complete optical test of the bearing surface is undertaken in parallel or sequentially such that defects existing on the bearing surface and/or component surface are reliably detected.

It is furthermore provided according to the invention that the tested bearing component is classified as defect free only when a defect free result is established in both partial testing steps. A defect free result is, of course, also to be understood in this context to mean that the detected and/or detectable defects lie below a still permissible tolerance limit. As is explained in still more detail below with the aid of the exemplary embodiment, this tolerance limit is also determined, among others, by the mechanisms and/or structures in the case of the formation of cracks caused by defects, in the respective specific material of the bearing components and the case of use.

In summary, the inventive method offers an elegant, non-destructive testing method, in particular for antifriction bearing components and, with particular preference, for antifriction bearing balls, which enables the highest possible reliability with regard to the component service life through the combination of two partial testing steps.

According to an advantageous refinement of the inventive method, the optical test is undertaken in automated fashion by means of a high speed camera. The latter can preferably record the respective actual surface condition and compare it, for example in digitized form, with a stored ideal surface condition. When there are significant deviations caused by defects, a negative test result is then reported.

The invention is further explained by way of example below with the aid of a drawing, the specific embodiments and examples represented not signifying any limitation of the invention. In the drawing:

FIG. 4 is a schematic of the cycle of the inventive method; and

Figure 1:
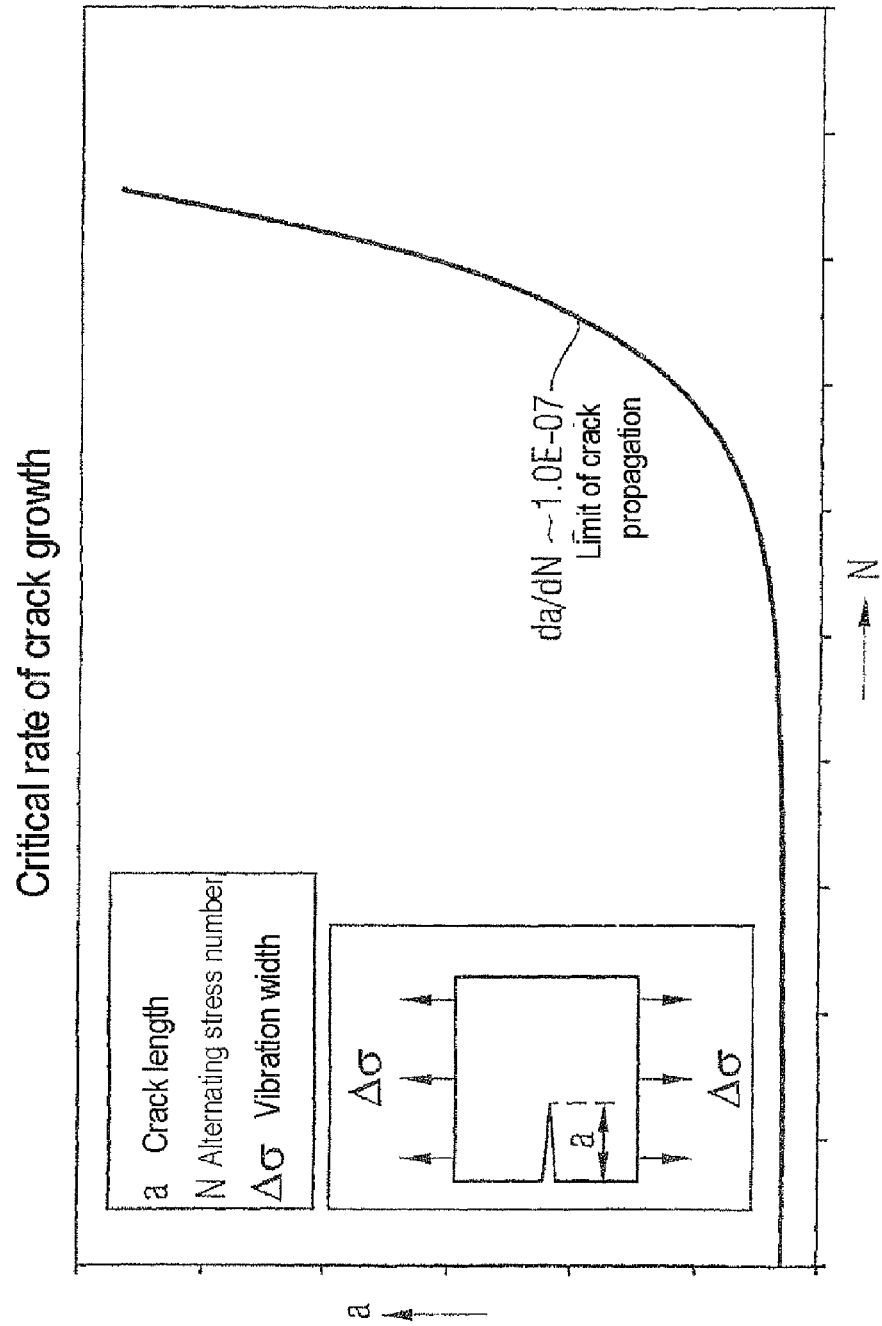
FIG. 1 shows, by way of example, for a basic understanding of the invention, the rate of growth of cracks as a function of the stress intensity factor in the case of vibrating stress.

FIG. 1 is a schematic of the critical rate of growth of cracks below or above the critical defect size/limit of the crack propagation, the crack length a being illustrated as a function of the load alternation number N. There is clearly a substantial rise in crack length (limit of the crack propagation; da/dN~10-7 load alternation). In other words comparatively small defects that firstly remain undetected can lead via the number of load alternations to a relatively sudden and then dramatic crack propagation.

Figure 2:
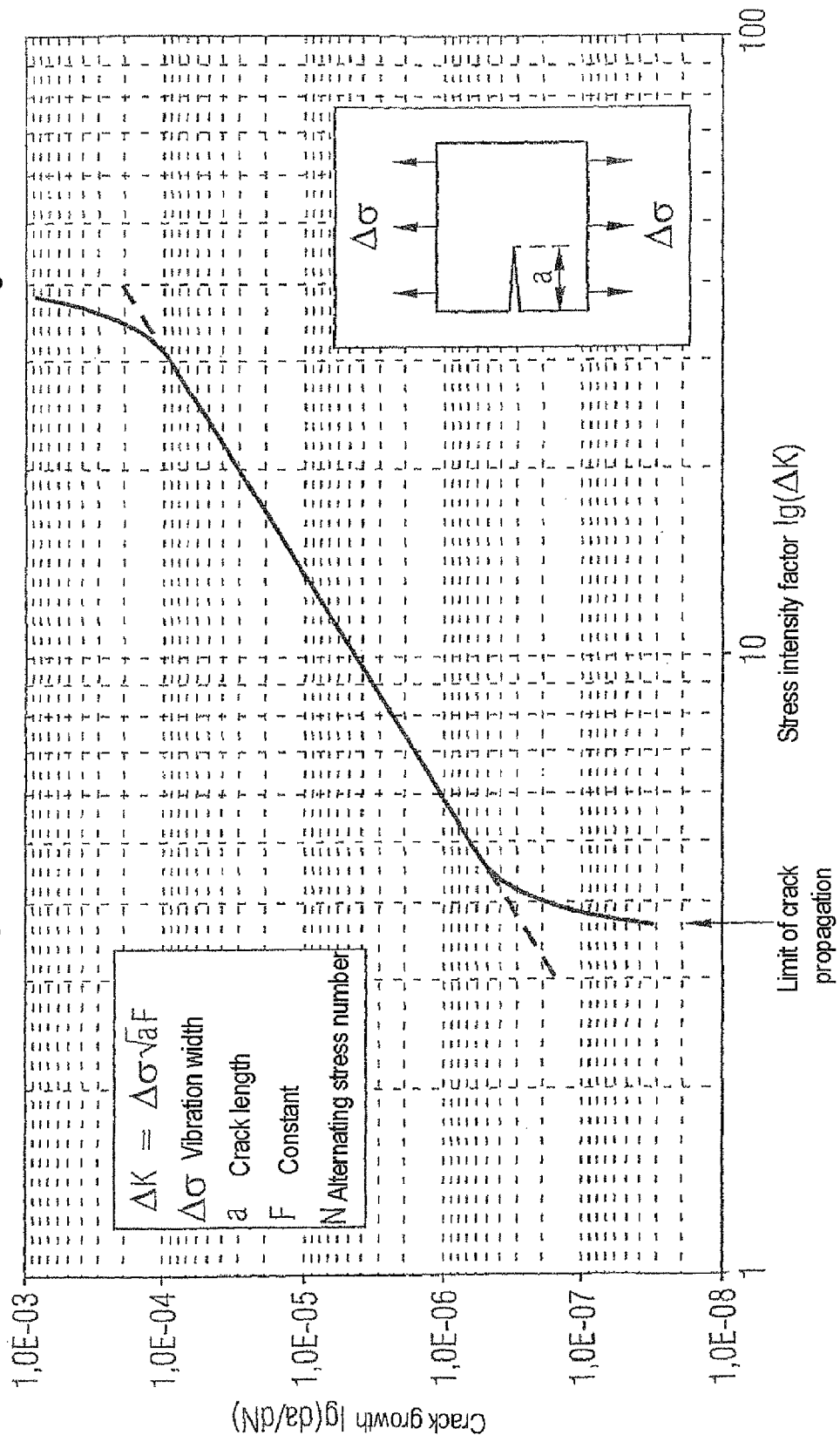
FIG. 2 is a schematic of the critical rate of growth of cracks.

For the purpose of further comprehension, FIG. 2 illustrates (logarithmically) that the crack growth Ig(da/dN) increases dramatically starting from the limit of the crack propagation, as a function of the stress intensity factor Ig($\Delta K$).

Thus, in the case of vibrating stress, it is possible to detect a substantially increased rate of crack growth starting from a specific stress intensity factor that is proportional to the vibration width or the square root of the crack length, in accordance with the formula $\Delta K = \Delta\sigma * \sqrt{a} * F$, where:

$\Delta\sigma$ Vibration width
a Crack length
F Constant
N Load alternation number.

Figure 3:
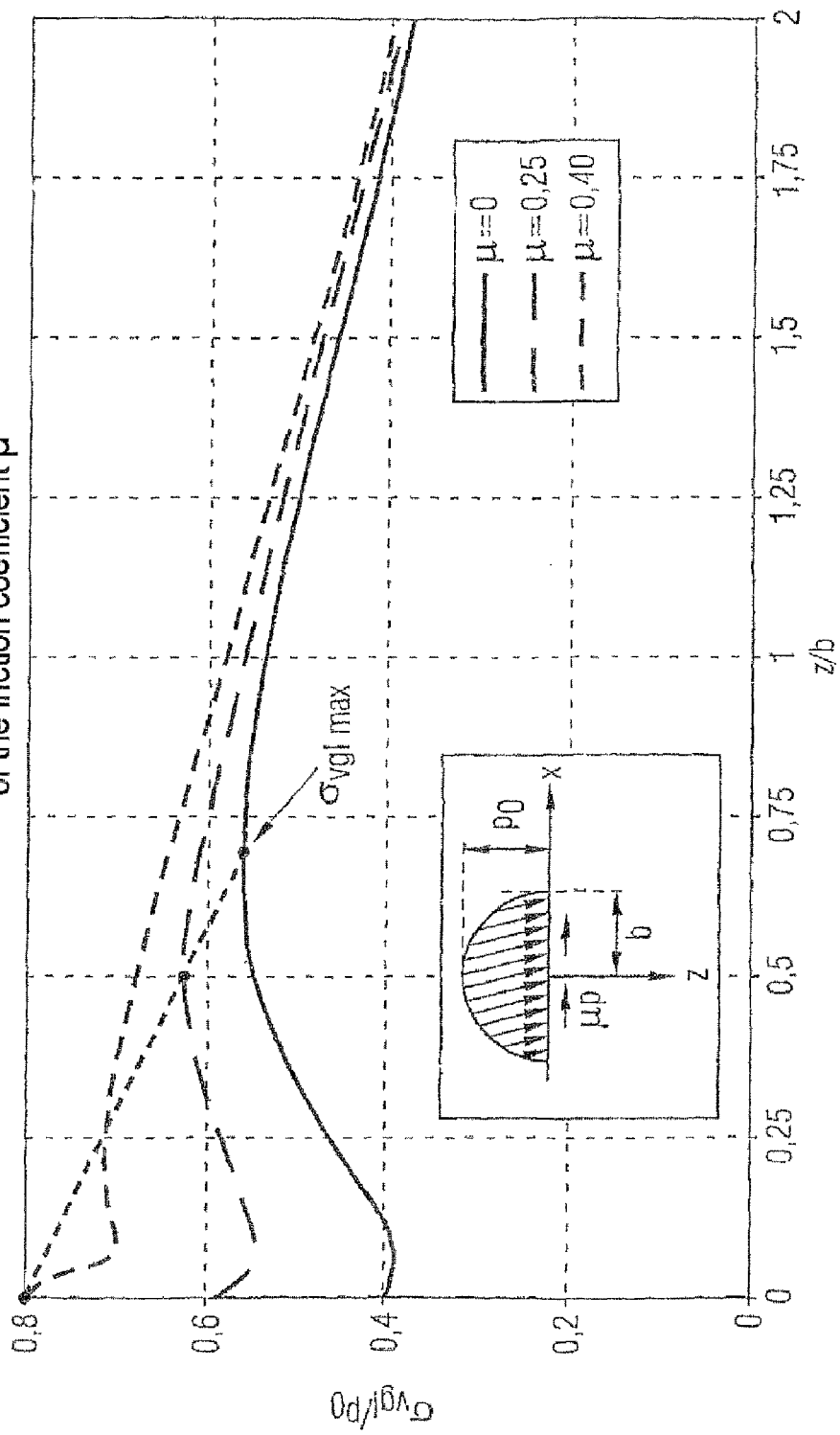
FIG. 3 shows reference stresses as a function of depth for various values of the friction coefficient.

FIG. 3 is a schematic of the variation in the position of the so-called point of maximum load (Pmax), which basically migrates in the direction of the bearing surface or component surface in the event of poor lubrication. Illustrated, by way of example, as a function of depth are the relationships or the position of the reference stress $\sigma_{vglmax}$ (point of maximum load) in relation to the pressure at the rolling contact $p_o$ for an ideal lubrication (friction coefficient $\mu=0$), a lubricating situation worsened, by way of example, by a lack of lubricant or overheating ($\mu=0.25$), and for a very poor lubrication ($\mu=0.4$). It is to be seen that the maximum reference stress/$p_0$ moves from a value of approximately 0.55 for a depth/width ratio z/b of the contact ellipse of approximately 0.7, via a reference stress value/$P_0$ of 0.62 at z/b≈0.5 to a reference stress value/$P_0$ of approximately at z/b≈0.0, the latter lying virtually directly in the bearing surface or below the component surface.

The respective positions of the point of maximum load are determined in this way for various operating parameters.

Against this background, the inventive method may now be described in detail in conjunction with FIGS. 4 and 5. A bearing component 1 in the form of a ball bearing ball is provided for testing at the start of the method. Parameters P1, P2, P3 . . . are available on the basis of the parameters both of the bearing component 1 (for example material, hardening, dimensioning etc.) and of the future operating conditions to be expected. Said parameters are used to determine the position of the point of maximum mechanical load $P_{max}$ from empirical values (compare FIG. 3 to this end, for example). This is illustrated in an enlarged fashion in FIG. 4 only schematically for an area 2 of the surface 3 of the ball bearing ball 1 (symbolized by a detail 5 symbolized in outline through a magnifying glass 6). This results in a material testing depth MPT within which point $P_{max}$ lies operationally.

Starting therefrom, in a first step the bearing component 1 is fed—like all remaining bearing components (not illustrated), for the purpose of attaining a perfect test—to a first partial testing step T1 in the form of an ultrasound test US.

In parallel or, (as in the exemplary embodiment illustrated) sequentially, the bearing component 1 is then fed to a second partial testing step T2, which comprises an optical test OP.

Figure 5:
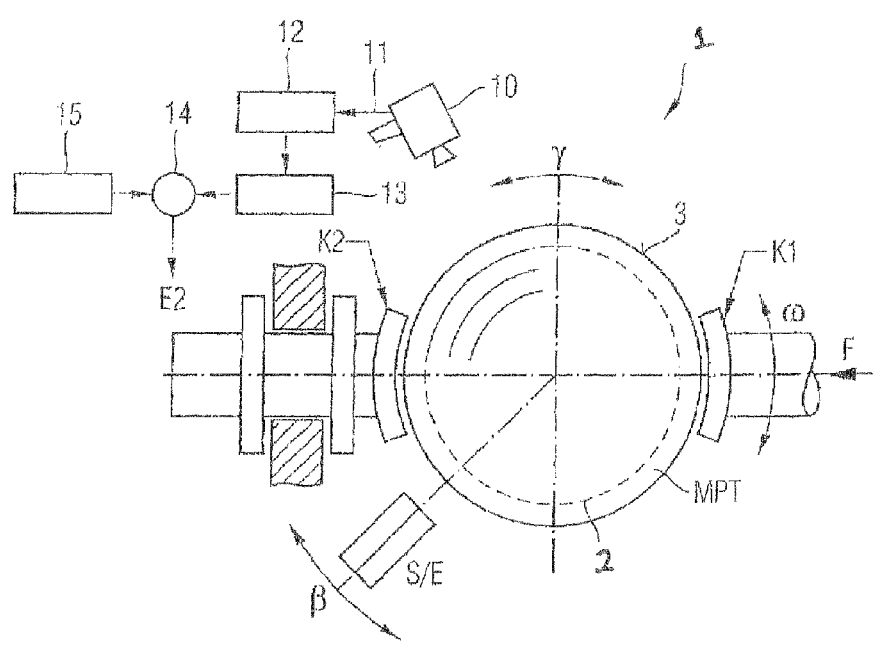
FIG. 5 shows a detail from FIG. 4.

As FIG. 5 shows in an enlarged illustration, one possibility of configuring the ultrasound test US is as follows: the bearing component 1 is pressed with a pressure force FA by an axially movable spherical cap K1 against a second, fixed spherical cap K2 and rotated with an angular velocity ω. Provided for the test is a combined ultrasound transmitter/receiver S/E that executes a swiveling movement by the angle β during testing. Since it is not possible in the case of this measurement to inspect the area of the bearing component 1 respectively covered by the spherical cap K1 or K2, a second measurement operation is carried out where in this case the bearing component is rotated by an angle γ by comparison with its first measured position such that it is now also possible to inspect the areas originally covered by the spherical caps K1, K2.

If no defect (in any case, however, no defect that lies above a permissible tolerance limit) is established inside the material testing depth MPT during this inspection, a positive test result E1 is generated and output.

In the second partial testing step, a complete optical test of the bearing surface 3 of the bearing component 1 is undertaken. In this case, a complete image of the bearing surface (surface) 3 is scanned by means of a high speed camera 10. As indicated merely schematically in FIG. 5, the high speed camera 10 can be arranged and/or moved such that it scans the bearing surface similar to the ultrasound test. The scanning result 11 therefore represents the actual surface condition 12 which—if appropriate, after digitization 13—is compared in a comparator 14 with the ideal surface condition 15 of an ideal bearing component. A positive test result E2 is yielded when no significant deviations identifying a defect are established.

The two test results E1 and E2 are combined in an evaluation logic 16 (FIG. 4), and a positive final test result E is generated only given the presence of two positive test results.

LIST OF REFERENCE SYMBOLS

1 Bearing component (ball bearing ball)
2 Area
3 Surface
5 Detail
6 Magnifying glass
10 High speed camera
11 Scanning result
12 Actual surface condition
13 Digitization
14 Comparator
15 Ideal surface condition
16 Evaluation logic
a Crack length
E Final test result
E1, E2 Test result
F Constant
FA Pressure force
K1 Spherical cap
K2 Spherical cap
MPT Material testing depth
N Load alternation number
OP Optical test
P1,P2,P3 Parameters
Pmax Point of the maximum mechanical load
S/E Ultrasound transmitter/receiver
T1 First partial testing step
T2 Second partial testing step
US Ultrasound test
$\beta$ Angle
$\gamma$ Angle
$\mu$ Friction coefficient
$\omega$ Angular velocity

The invention claimed is:

1. A method for testing a bearing component of a bearing in which a bearing surface and a load bearing area located below the bearing surface must exhibit complete freedom from defect, the method comprising the following steps:

determining a material testing depth of the bearing component within which material testing depth a point of maximum mechanical load occurring during operation lies;

subjecting the bearing component to an ultrasound test in a first partial testing step to test the load bearing area located beneath the bearing surface for defects by means of ultrasound, at least to the material testing depth;

undertaking a complete optical test of the bearing surface in which an actual surface condition of the bearing surface is compared with a desired surface condition of the bearing surface; and classifying the bearing component as defect free only when both the first partial testing step and the second partial testing step yield a defect free result.

2. The method as claimed in claim 1, wherein an optical test is undertaken in automated fashion by means of a high speed camera.

* * * * *